United States Patent [19]

Chow et al.

[11] Patent Number: 4,966,138
[45] Date of Patent: Oct. 30, 1990

[54] PUNCTURE PROTECTOR

[76] Inventors: Peter P. Chow; Josephine N. Lo; Loren A. Chow, all of 2317 Byrnes Rd., Minnetonka, Minn. 55343

[21] Appl. No.: 330,419

[22] Filed: Mar. 29, 1989

[51] Int. Cl.$^5$ .............................................. A61L 15/00
[52] U.S. Cl. .................................... 128/155; 128/156; 206/447
[58] Field of Search ..................... 128/155, 91 R, 888, 128/156, 889; 206/447

[56] References Cited

U.S. PATENT DOCUMENTS

| | | |
|---|---|---|
| 2,170,147 | 8/1939 | Lane ...................................... 206/447 |
| 4,126,130 | 11/1978 | Cowden et al. .................. 128/91 R |
| 4,285,338 | 8/1981 | Lemelson ........................... 128/155 |
| 4,559,042 | 12/1985 | Votel . |
| 4,717,386 | 1/1988 | Simmons . |
| 4,758,229 | 7/1988 | Doerschner . |
| 4,767,412 | 8/1988 | Hymanson . |

Primary Examiner—Richard J. Apley
Assistant Examiner—N. Paul
Attorney, Agent, or Firm—Kinney & Lange

[57] ABSTRACT

A puncture protector having a flexible backing with adhesive on one side thereof and a shielding arrangement for blocking passage of needles, both of which can be conformed to that portion of the body of the needle user, often the fingers, which is desired to be protected.

8 Claims, 2 Drawing Sheets

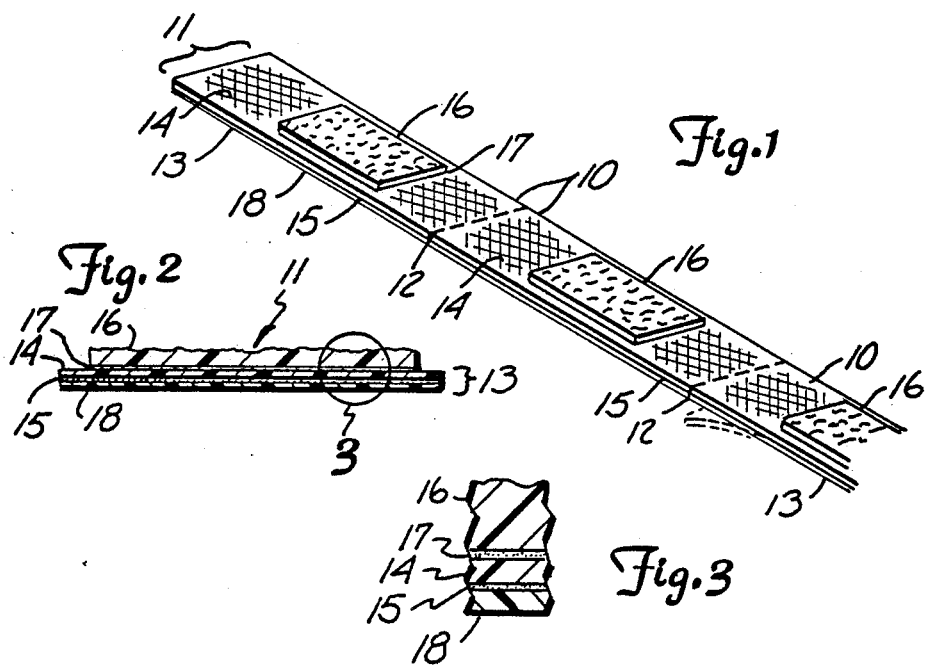
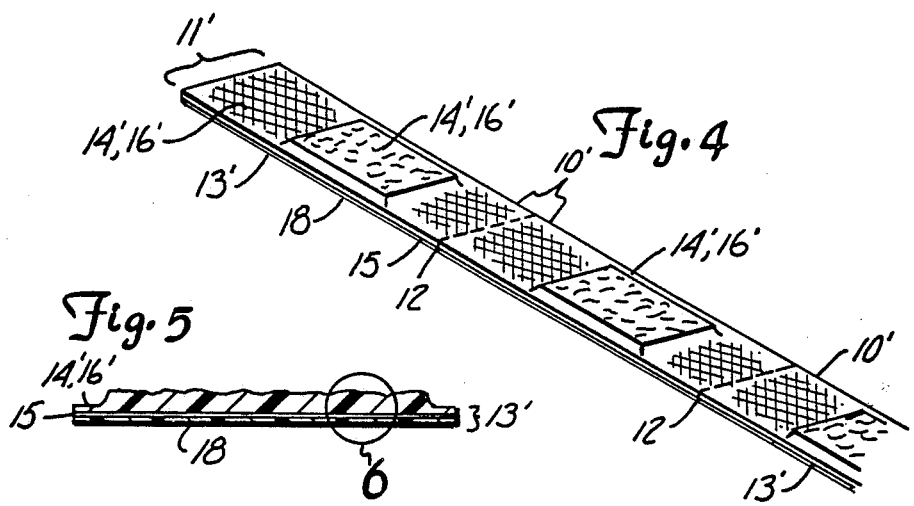

PUNCTURE PROTECTOR

BACKGROUND OF THE INVENTION

This invention relates to protectors to be positioned on a user's body to protect against puncture wounds thereof and, more particularly, conformable body protectors which can protect against puncture wounds due to the manipulation of syringes having a needle thereon and of such syringe needles.

Many diseases can be transmitted to others if tissue or fluids taken from one already suffering from such a disease are somehow introduced into another's body. Health care providers, such as physicians, nurses or medical technicians, are among those most likely to be in contact with people afflicted with such diseases. In carrying out their duties, such care providers often draw blood samples from, or inject medications into, the bodies of such disease sufferers for various reasons, or they must in some manner manage other operations with the resulting samples in the course of performing their duties.

Such samples are often obtained through the use of syringes fitted with a corresponding needle. Samples so obtained are often injected into a container of some sort in preparation for testing or as part of the various testing operations. During the various manipulations in these procedures, and in medication injection procedures, the persons involved therewith, including the above care providers, run the risk of being accidentally punctured in a finger, or elsewhere in their bodies, by the sharply pointed tips of the needles used in such sampling or medicating syringes. Such a puncture leaves a painful wound and can carry with it a substantial risk of infection to one so punctured, thereby exposing one so injured to the possibility of subsequently suffering the same disease as the person in whom the needle involved was first inserted.

Thus, some kind of protective arrangement is often desired for use by those persons directly involved during these kinds of procedures. However, many of the protectors currently in use are intended to be placed directly around a needle or around an entire syringe with its needle. These kinds of protectors often cannot be used at the time the protection is most needed, during various manipulations of a syringe fitted with a needle or manipulations of just a needle. Other existing protectors which can be used by a person performing such manipulations are often clumsy and ill suited for someone required to accomplish what are often delicate and intricate maneuvers, or they are independent entities which can be easily separated from the location in which they are needed. Thus, there is desired a protector for the person, using a syringe needle in situations carrying some risk of disease if an accidental puncture should occur, which avoids these problems.

SUMMARY OF THE INVENTION

The present invention provides a puncture protector having a flexible backing with adhesive on one side thereof and a shielding arrangement for blocking passage of needles, both of which can be conformed to that portion of the body of the needle user, often the fingers, which is desired to be protected. The flexible backing is sufficiently flexible to permit various body movements during its use. Dispensing arrangements are provided so that the protectors are easily obtained at selected operating stations.

BRIEF DESCRIPTION OF THE DRAWINGS

FIG. 1 shows a pictorial view of an embodiment of the present invention,

FIG. 2 shows a cross section view of a portion of FIG. 1,

FIG. 3 shows a fragmentary portion of FIG. 2,

FIG. 4 shows a pictorial view of an alternative embodiment of the present invention, FIG. 5 is a cross section view taken in FIG. 4, FIG. 6 is a fragmentary view of a portion of FIG. 5.

DETAILED DESCRIPTION OF THE PREFERRED EMBODIMENTS

Figure 7:
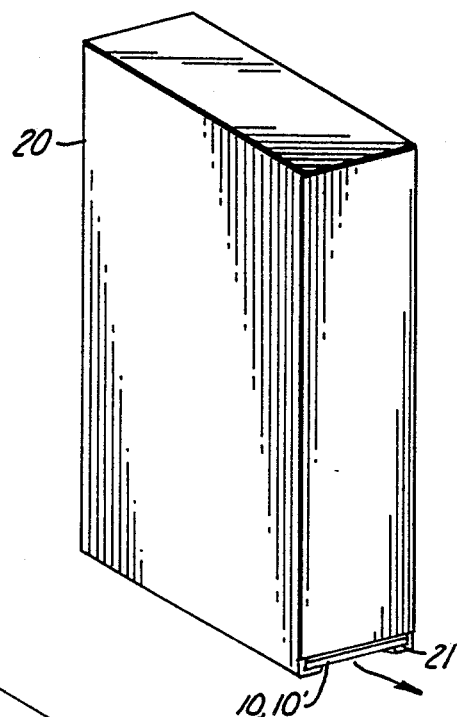
FIG. 7 is a pictorial view of an arrangement for providing an access for the present invention.

A series of easily positionable body puncture protectors, 10, are shown in FIG. 1 in the form of a strip, 11, containing this series connected one after the other end-to-end. Though useful for protecting bodily parts generally against accidental needle punctures, puncture protectors 10 are especially useful for protecting fingers, which are the bodily portions having the greatest risk. The shape of each of protectors 10 shown in FIG. 1 is especially adapted for use with the fingers of one handling a syringe, these being body parts which are often in the vicinity of the intended point of insertion of a syringe needle for purposes of guiding same in that operation, a situation leading to such greater risk. Other shapes may be used for a protector 10 intended for covering other body portions if so desired.

Strip 11 of FIG. 1, formed by those end-to-end connected protectors 10 shown there, can be formed continuously with a portion at each of the joints, 12, between each of protectors 10 weakened in an appropriate manner to permit separation of one from the next by a user desiring to obtain such a protector. This weakened portion at each joint 12 can be provided in many ways, such as by a series of perforations through the flexible backing, e.g. those indicated by the dashed lines shown at each of joints 12.

The perforations at joints 12, or other weakening measures, are applied to a backing material arrangement, 13, which is formed of a sufficiently flexible and pliant strip of material to permit this material to be conformed to a human finger. Backing material 13 is primarily formed from a thin sheet, 14, of a suitable polymer such as polyethylene. The perforations or other weakening means at joints 12 serve to define separate portions in sheet 14 for each of body protectors 10.

Polymer strip 14 has provided, on the under side thereof in FIG. 1, a pressure-sensitive adhesive, 15. Adhesive 15 permits the securing of polymer strip 14 to a human finger or other body portion.

The upper surface of polymer strip 14 for each of the portions thereof separately defined by joints 12 has a flexible shield member, 16, bonded thereto by a suitably pliable adhesive, 17, to complete each of protectors 10. Shield 16 must also be impervious to punctures by syringe needles. Thus, when protector 10 is properly positioned so that shield 16 is between any body portions sought to be protected, such as a finger subject to risk of puncture by a syringe needle during manipulation thereof, shield 16 will intercept such a needle preventing it from any significant further travel toward the portion of the finger protected.

Shield 16 is formed of a tough but flexible polymer material which again can be polyethylene, though thicker than that used for strip 14, but other suitable polymers can alternatively be used. This shield material must be sufficiently flexible to permit at least reasonable conformance of protector 10 about the finger of a user.

The surface of polymeric layer 14 on which shield 16 is bonded has those exposed portions thereof, where shield 16 is not bonded, roughened or ribbed so that some parts thereof protrude with respect to others. This improves the user's grip of objects the user may be handling during the wearing of body protector 10.

Finally, a covering sheet is placed against adhesive 15 on the bottom side of polymeric layer 14 to prevent its being contaminated before use and to prevent its unwanted adherence to other objects. This covering sheet, 18, can conveniently be a coated paper. Coated paper 18 can be perforated along with sheet 14 in forming the weakened portions at joints 12.

FIG. 2 shows a cross section of a portion of FIG. 1, and provides substantially more of the details of the construction and constituents of finger puncture protector 10. A fragmentary view is shown in FIG. 3 of a portion of FIG. 2 providing a further improvement in the viewing of the details of that structure. The numerical designations used in FIGS. 2 and 3 designate the same structures there that they designated in FIG. 1.

FIG. 4 shows an alternative embodiment of the strip of body puncture protectors shown in FIG. 1. The features that have changed in FIG. 4 from FIG. 1 retain the same numbers they had in FIG. 1 at present, but with a prime symbol provided thereafter. Those features which have not changed retain the same designations in FIG. 4 as they had in FIG. 1.

Thus, finger puncture protectors 10 in FIG. 1 are designated 10' in FIG. 4, and the strip in FIG. 4 is generally designated 11'. The difference in FIG. 4 of strip 11' from strip 11 in FIG. 1 is the forming of polymeric strip 14 in FIG. 1, as part of backing layer 13, in a single unit with shield 16 in FIG. 1 to form the integrated polymeric strip 14', 16' in FIG. 4.

Puncture protectors 10' in strip 11' are again separable at joints 12 by a weakening therein which again conveniently is provided by a series of perforations of backing material 13'. Cover sheet 18 is again placed against adhesive 15 on the lower side of integrated polymeric strip and shield combination 14', 16'. The portions of the upper surface of integrated combination 14', 16' where the raised shield portion is not present are again roughened or ribbed. The forming of an integral polymeric strip and shield combination 14', 16' can be desirable in reducing the costs of protectors 10' compared with those of protectors 10 through reducing the number of fabrication steps.

FIG. 5 again is a cross section view taken in FIG. 4 showing the construction and the constituents of protectors 10' in greater detail. Also again, the fragmentary view of FIG. 6 taken from FIG. 5 gives a view in greater detail yet of that construction. The numerical designations used in FIGS. 5 and 6 to denote the structural features shown there are those used to designate those same structures in FIG. 4.

Integrated polymeric strip and shield combination 14', 16' again must be sufficiently flexible to be reasonably conformable to a user's body portion, such as a finger. The raised portion thereof serving as a shield must again be impervious to syringe needle impacts to provide adequate protection for the body portion therebeneath. Once again, a suitable polymeric material may be used, and again can be polyethylene, though other kinds of polymers are suitable alternatives.

A location at a medical facility where procedures requiring the use of syringes fitted with needles are being performed are often busy locations. This situation means that a puncture protector must be quickly and easily available to one who is about to use a needle, or a syringe with a needle, to promote efficiency and to encourage use. As a result, a convenient dispensing arrangement will be a significant aid in assuring use of such puncture protectors during the handling of syringes with needles, or the handling of just needles.

A very economical dispenser is shown in FIG. 7, and is based on having puncture protectors 10 or 10' actually separated from strips 11 or 11', respectively, in which they are manufactured. These separated protectors are then stacked in a container, 20, having an opening at the bottom, 21. Opening 21 on the bottom of container 20 extends back from the side portion of that opening in FIG. 7 to thereby permit the tip of a user's finger to be placed against a protector 10. Once so positioned, the finger can slide a protector 10 or 10' out the side facing portion of opening 21 for use. Gravity pulls down the ones of protectors 10 or 10' remaining in the stack in container 20 to position the next one in opening 21.

Figure 8:
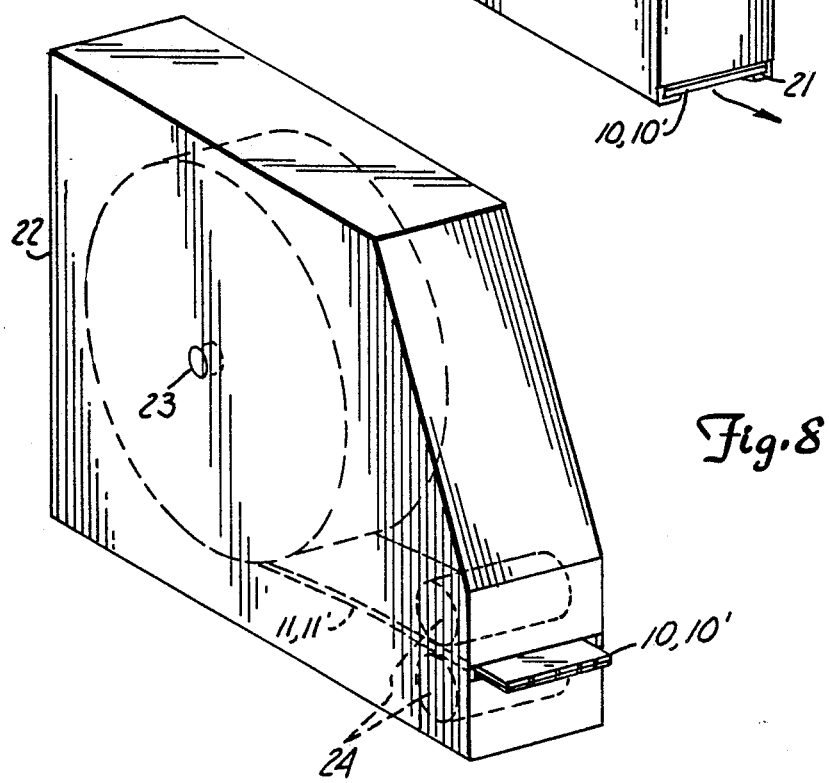
FIG. 8 is a pictorial view of an alternative arrangement for providing an access for the present invention.

Alternatively, a dispenser that exposes more of a body puncture protector, or finger puncture protector, 10 or 10' permits a user to more quickly grasp same to correspondingly improve convenience. A dispenser, 22, providing such a result is shown in FIG. 8 where a strip 11 or 11' of protectors 10 or 10', respectively, has been wound into a coil and mounted on a spindle, 23, in dispenser 22. The outer end of that coil has been placed between two friction rollers, 24, which operate with detentes to permit one protector 10 or 10' to be pulled out at a time to then be torn off from the strip in which it was provided. Dispenser 22 provides a way to quickly acquire a protector 10 or 10' for subsequent application to a user's finger.

Thus, protectors 10 or 10', as protectors for protecting bodily portions such as fingers against punctures by syringe needles, can be made quickly and conveniently available to a person manipulating such needles, whether individually or while mounted on corresponding syringes. Such convenience and quickness avoids discouraging a user from applying such a protector to that part of the body of that user which is at risk during these manipulations, and so encourages safe practices.

Although the present invention has been described with reference to preferred embodiments, workers skilled in the art will recognize that changes may be made in form and detail without departing from the spirit and scope of the invention.

What is claimed is:

1. A conformable body protector for protecting selected portions of a user's body, such as fingers, against needle punctures thereof when that user is manipulating needles both individually and as mounted on syringes, said body protector comprising:

a flexible backing material portion capable of substantial flexure to be able to conform to a selected portion of said user's body, and having first and second sides thereof opposite one another with a releasable adhesive provided on said first side thereof; and a shield member portion capable of blocking passage therethrough of syringe needles forced thereagainst, said shield member portion also being capable of substantial flexure to permit substantial conformance thereof to that portion of said user's body against which said flexible backing material portion is to be conformed, said shield member portion being adherent to all of a substantial portion of said flexible backing material portion which is covered by said shield member at a selected location therein.

2. The apparatus of claim 1 wherein said second side of said flexible backing material portion has surface portions protruding with respect to other surface portions in those parts of said second side at locations other than where said shield member portion is located.

3. The apparatus of claim 1 which further comprises a plurality of body protectors each comprising:

a flexible backing material portion capable of substantial flexure to be able to conform to a selected portion of said user's body, and having first and second sides thereof opposite one another with a releasable adhesive provided on said first side thereof; and a shield member portion capable of blocking passage therethrough of syringe needles manually forced thereagainst, said shield member portion also being capable of substantial flexure to permit conformance thereof to that portion of said user's body against which said flexible backing material portion is to be conformed, said shield member being adherent to said flexible backing material portion; and wherein said plurality of body protectors are joined end-to-end so that each is joined with two others, one at each end thereof, except for a first and a last one thereof, said plurality of body protectors together thereby forming a connected strip of body protectors, those locations where each of said body protectors is joined to another being weakened to thereby permit one to be relatively easily torn there from another to which it is attached.

4. The apparatus of claim 1 which further comprises a plurality of body protectors each comprising:

a flexible backing material portion capable of substantial flexure to be able to conform to a selected portion of said user's body, and having first and second sides thereof opposite one another with a releasable adhesive provided on said first side thereof; and a shield member portion capable of blocking passage therethrough of syringe needles manually forced thereagainst, said shield member portion also being capable of substantial flexure to permit conformance thereof to that portion of said user's body against which said flexible backing material portion is to be conformed, said shield member portion being adherent to said flexible backing material portion; and said plurality of body protectors being stacked in a container having an opening at one end thereof exposing and permitting one of said plurality of body protectors to be removed therefrom, which after any removal thereof is replaced in said opening by another of said plurality of body protectors exposing and permitting it to be removed until all of said plurality of body protectors have been removed from said container.

5. The apparatus of claim 1 wherein a cover sheet is provided over said releasable adhesive on said first side of said backing material.

6. The apparatus of claim 1 wherein said shield member portion is an integral part of said flexible backing material portion.

7. The apparatus of claim 1 wherein said shield member portion is secured to said second side of said flexible backing material.

8. The apparatus of claim 4 wherein said strip is coiled and provided in a dispenser means presenting one of said plurality of body protectors in an opening thereof so that a user can tear it off at said weakened portion where that body protector remains attached to a succeeding one of said plurality of body protectors, said succeeding one of said plurality of body protectors being next presented at said opening in said dispenser.

* * * * *